United States Patent
Speier et al.

(10) Patent No.: US 12,076,111 B2
(45) Date of Patent: Sep. 3, 2024

(54) USING CARDIAC MOTION FOR BEAT-TO-BEAT OPTIMISATION OF VARYING AND CONSTANT FRACTIONS OF CARDIAC CYCLES IN SEGMENTED K-SPACE MRI ACQUISITIONS

(71) Applicants: Siemens Healthineers AG, Forchheim (DE); Guy's & St. Thomas' NHS Foundation Trust, London (GB)

(72) Inventors: Peter Speier, Erlangen (DE); Peter Gatehouse, London (GB)

(73) Assignees: Siemens Healthineers AG, Forchheim (DE); Guy's & St. Thomas' NHS Foundation Trust, London (GB)

( * ) Notice: Subject to any disclaimer, the term of this patent is extended or adjusted under 35 U.S.C. 154(b) by 0 days.

(21) Appl. No.: 17/896,221

(22) Filed: Aug. 26, 2022

(65) Prior Publication Data
US 2023/0072744 A1    Mar. 9, 2023

(30) Foreign Application Priority Data
Aug. 31, 2021    (EP) .................................. 21194078

(51) Int. Cl.
  *A61B 5/00*    (2006.01)
  *G01R 33/563*  (2006.01)
  *G01R 33/567*  (2006.01)
(52) U.S. Cl.
  CPC .......... *A61B 5/0044* (2013.01); *A61B 5/7285* (2013.01); *G01R 33/56325* (2013.01); *G01R 33/5673* (2013.01); *G01R 33/5676* (2013.01)

(58) Field of Classification Search
  CPC ................ A61B 5/0044; A61B 5/7285; G01R 33/56325; G01R 33/5673; G01R 33/5676
  See application file for complete search history.

(56) References Cited

U.S. PATENT DOCUMENTS

| | | | | |
|---|---|---|---|---|
| 5,997,883 A | * | 12/1999 | Epstein | A61B 5/7292 600/439 |
| 6,192,273 B1 | * | 2/2001 | Igel | A61B 5/363 600/518 |
| 7,945,304 B2 | | 5/2011 | Feinberg | |
| 10,405,772 B2 | * | 9/2019 | Korosec | G01R 33/5635 |

(Continued)

FOREIGN PATENT DOCUMENTS

EP    3413075 A1    12/2018

OTHER PUBLICATIONS

Chung, S. et al: "Improved Method for Retrograde Gating for Cardiac Magnetic Resonance Imaging", Proc. Intl. Soc. Mag. Reson. Med. 20 (2012), S. 3853.

(Continued)

*Primary Examiner* — Dixomara Vargas
(74) *Attorney, Agent, or Firm* — Harness, Dickey & Pierce, P.L.C.

(57) ABSTRACT

A method for adapting, per cardiac cycle, the parameters governing interpolation of varying and non-interpolation of fixed fractions of each individual cardiac cycle is provided. A time series of data values associated with a cardiac cycle is received, and the time series is scaled to a reference cardiac cycle, wherein the scaling includes applying a model to the time series to generate a scaled time series of data values associated with the first cardiac cycle. The model is trained using the scaled time series.

22 Claims, 8 Drawing Sheets

(56) References Cited

U.S. PATENT DOCUMENTS

| | | | |
|---|---|---|---|
| 2012/0101541 A1* | 4/2012 | Corbucci | A61N 1/395 |
| | | | 600/509 |
| 2013/0006096 A1 | 1/2013 | Madore | |
| 2016/0228014 A1 | 8/2016 | Witschey et al. | |
| 2016/0242663 A1* | 8/2016 | Jayan | A61B 5/318 |
| 2018/0353139 A1* | 12/2018 | Speier | A61B 5/725 |
| 2019/0008480 A1* | 1/2019 | Gerard | A61B 8/5223 |
| 2019/0175052 A1* | 6/2019 | Forman | A61B 5/742 |
| 2020/0237314 A1* | 7/2020 | Qu | A61B 5/283 |
| 2021/0128076 A1* | 5/2021 | Shi | A61B 6/541 |
| 2022/0054021 A1* | 2/2022 | Batzer | A61B 5/7289 |
| 2023/0079852 A1* | 3/2023 | Speier | A61B 5/7289 |

OTHER PUBLICATIONS

Cardiac function and PA pressure https://web.archive.org/web/20200811215706/https://echobasics.de/diastole-en.html (Stand:Aug. 11, 2020).

Wikipedia—Isovolumetric contraction: https://web.archive.org/web/20190502072505/https://en.wikipedia.org/wiki/Isovolumetric_contraction (Stand:May 2, 2019).

Chung S. et al: "Duration of diastole and its phases as a function of heart rate during supine bicycle exercise", Am J Physiol Heart Circ Physiol 287: H2003-H2008, 2004.

The Wayback Machine: "Blood Flow", https://web.archive.org/web/20200810145850/http://www.rnceus.com/hemo/bloodflo2.htm, (Stand: Aug. 4, 2022).

\* cited by examiner

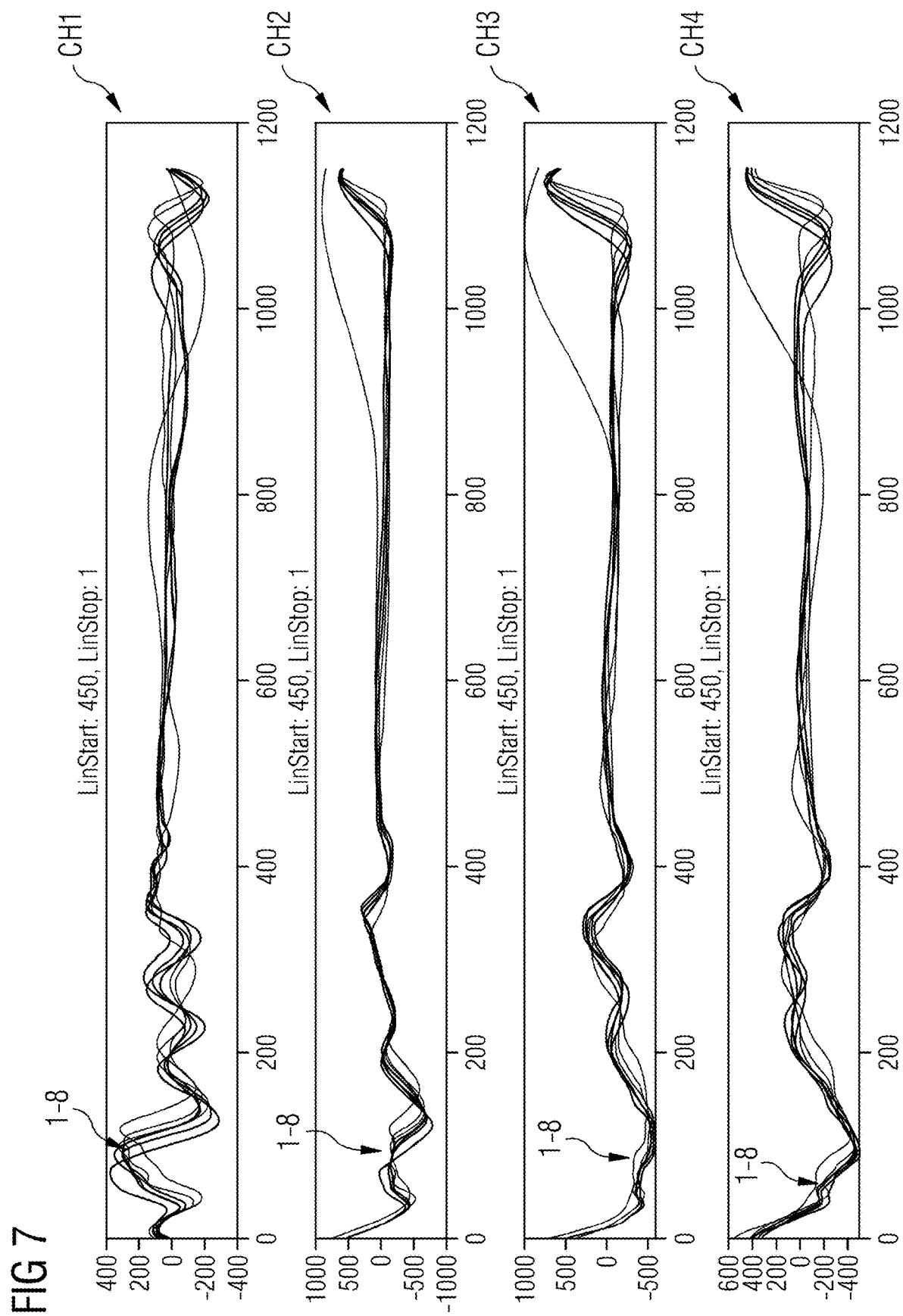

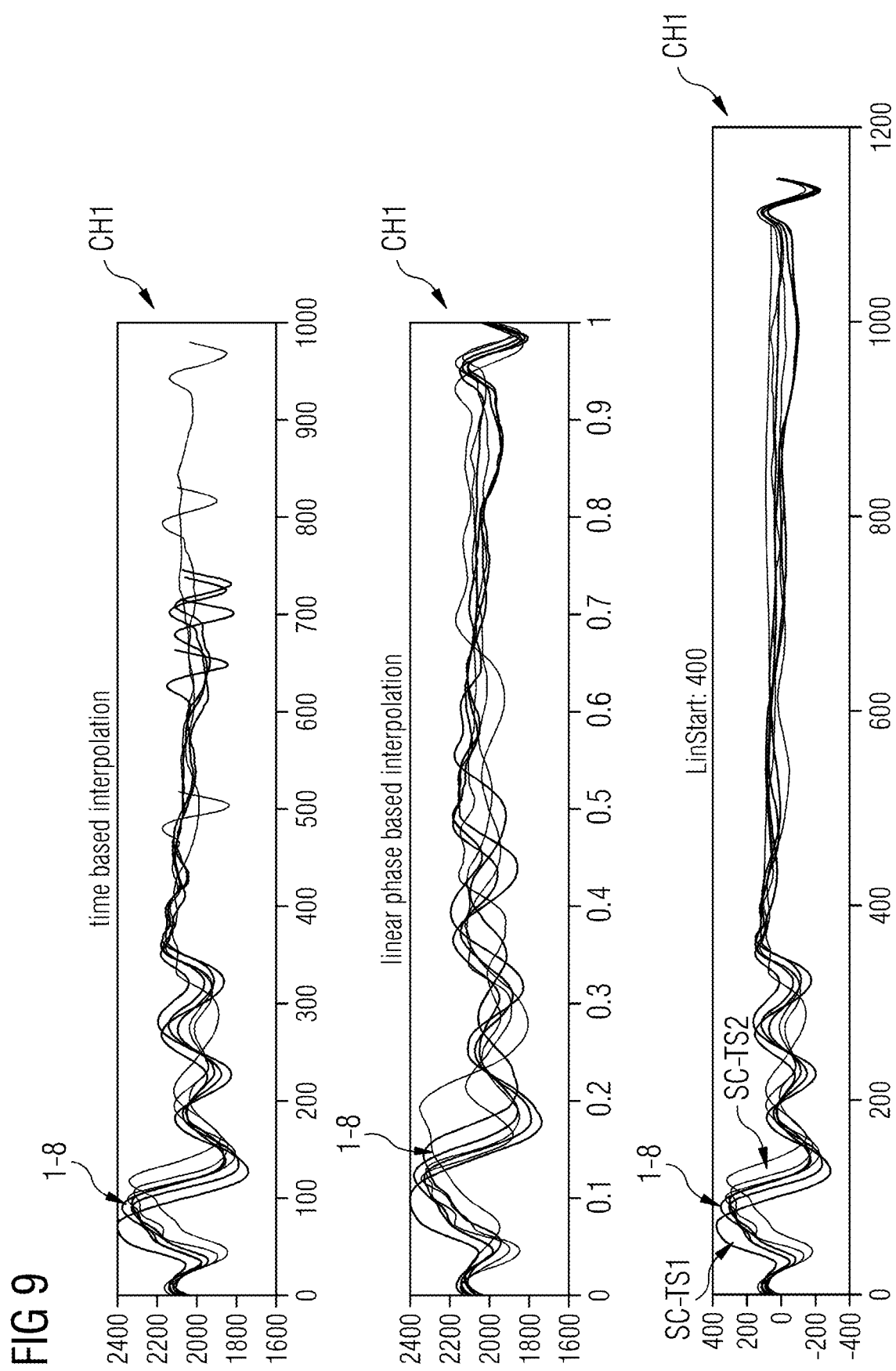

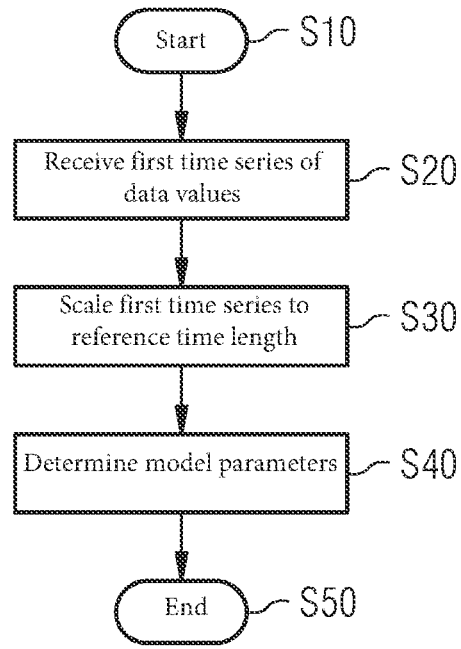
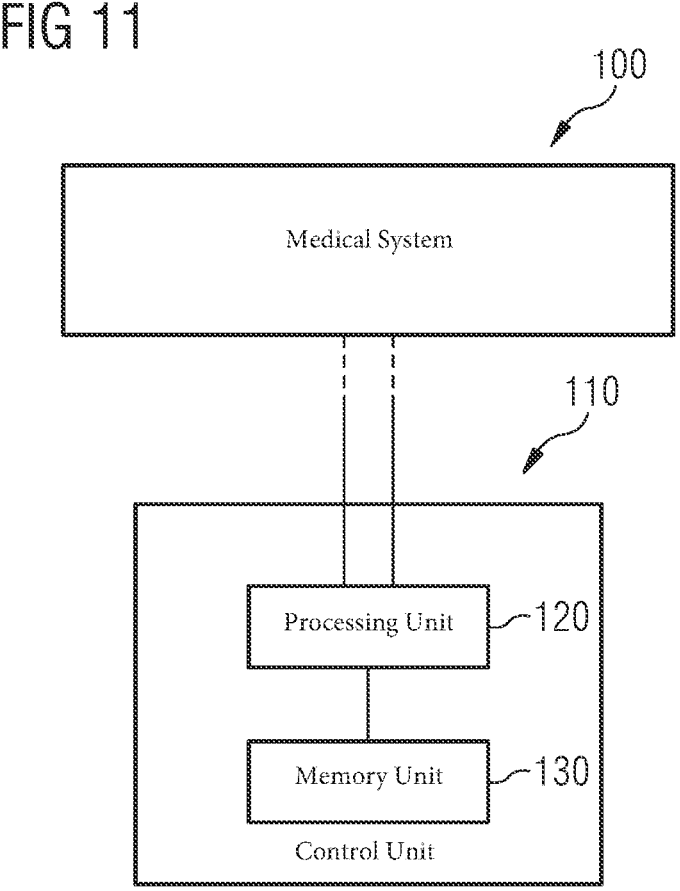

USING CARDIAC MOTION FOR BEAT-TO-BEAT OPTIMISATION OF VARYING AND CONSTANT FRACTIONS OF CARDIAC CYCLES IN SEGMENTED K-SPACE MRI ACQUISITIONS

CROSS-REFERENCE TO RELATED APPLICATION(S)

The present application claims priority under 35 U.S.C. § 119 to European Patent Application No. 21194078.8, filed Aug. 31, 2021, the entire contents of which are incorporated herein by reference.

FIELD

Various examples generally relate to cardiac phase interpolation, and specifically to a method for adapting a cardiac phase interpolation model per cycle of data using an Electrocardiography (ECG) measurement signal. Furthermore, a corresponding medical system, a computer program product, and an electronically readable data carrier are provided.

BACKGROUND

Cardiac MRI requires synchronization with cardiac motion to avoid image artefacts like blurring or phase-encode ghosting of cardiac tissue. For synchronization a trigger signal related to the cardiac motion is used. This signal can be generated by different sources; in clinical use it is usually the Electrocardiography (ECG), or Photoplethysmography if necessary. More experimental techniques exist, e.g., acoustic triggering or Pilot Tone. A diagnostic ECG contains multiple waves, which can be used as markers to separate weakly and strongly scaling fractions of each cardiac cycle. The P-wave corresponds to the start of the weakly scaling interval, but there is no precise electrical activity marking of the end of this interval. Therefore, even a diagnostic quality ECG could not be used by itself to precisely determine cardiac phases, in particular in patients with strongly arrhythmic cardiac cycles.

SUMMARY

Therefore, the idea of one or more example embodiments of the presented approach is to provide advanced techniques for cardiac phase interpolation, which overcome or mitigate at least some of the limitations and disadvantages mentioned.

This task is solved by the features of one or more example embodiments of and/or the independent claims. Further advantageous examples are included in the dependent claims.

In the following, the solution according to one or more example embodiments of the present disclosure will be described with regard to the claimed methods as well as with regard to the claimed medical systems, wherein features, advantages, or alternative embodiments may be assigned to the other claimed objects, and vice versa. In other words, the claims for the systems may be improved by features described or claimed in the context of the methods, and the claims of the methods may be improved by features describe in the context of the medical systems. In this regard, the functional features of the methods may be performed by respective operative units of the corresponding medical systems.

A computer-implemented method, i.e. for determining a cardiac phase interpolation model, comprises the following steps.

In a step, a series, or time series of data values of an ECG measurement signal associated with a first cardiac cycle is received. In various examples, the first cardiac cycle may be an arbitrary cardiac cycle of a plurality of cardiac cycles, over which a measurement is performed.

In various examples, a time series of data values, or measurement values, may refer to a cardiac motion information data, and may represent a complete ECG measurement data signal, which includes or comprises characteristics of a cardiac motion of a patient, specifically of a magnetohydrodynamic (MHD) effect in a patient. The data value might also be other motion information such as a (non-NMR based) RF sensor of cardiac motion integrated into MRI systems and known as BeatSensor. A data value may be associated with a corresponding time value, or more generally may be associated with an index value or a value on a scale representing a time scale of the ECG measurement. It is to be understood, that a time series should also apply to a series of data values, wherein the data values are associated with a further index values representing a chronologically sequential order. In particular, a time value may correspond to a point in time on a time scale of the performed ECG measurement.

In various examples, a plurality of measurement data values, i.e. a time series, or series, of data values, or in more general a plurality of sorted or indexed of data values, may be received which includes a group of data values associated with a first cardiac cycle and/or a further group of data values associated with the second cardiac cycle. In this regard, a time series may in general be referred to as a sorted or indexed series of data values. The cardiac cycles may be differentiated from each other by a trigger characteristic in the periodic signals associated with a cardiac cycle. In other embodiments, a separate time series may be received for at least one cardiac cycle. A time series may be referred to as a measurement signal, which may include signal characteristics correlated with cardiac motion. A time series may include a cardiac cycle, each cardiac cycle having essentially the same cardiac phases, however in different time periods or indices during a cardiac cycle.

In a further step, the first time series is scaled onto a reference cardiac cycle, wherein a time length of the first cardiac cycle is scaled to a reference time length of a reference cardiac cycle.

In various examples, a reference cardiac cycle may be received, or determined from the plurality of cardiac cycles. For example, a time series of data points associated with a reference cardiac cycle may be received, or the reference cardiac cycle may be determined from the plurality of cardiac cycles, over which the measurement is performed. The reference cardiac cycle may be a cardiac cycle which is not scaled, or an average cardiac cycle of the plurality of cardiac cycles, which may have an average time length. In this regard, the reference cardiac cycle may be the cardiac cycle to which other cardiac cycles are scaled to. In other words, after selection of the reference cycle, by applying the model to the time series associated with the other cardiac cycles, scaled time series associated each of them are generated, with the aim of optimally aligning the partial MRI data of all phases of motion of the heart's motion in each cycle.

Scaling comprises applying a model to the first time series (TS1), in order to generate a first scaled time series (SC-TS1) of data values associated with the first cardiac cycle.

In another step, model parameters of the model are determined based on, or using, the first scaled time series. Determining model parameters of a model may be generally referred to as improving or training the model.

The model parameters may be determined based on a difference between the first scaled time series and a time series of data values associated with the reference cardiac cycle.

The method may further comprise receiving a second time series of data values associated with a second cardiac cycle. Scaling the second time series onto the reference cardiac cycle, in the same way as the first cardiac cycle, wherein scaling comprises applying the model to the second time series, in order to generate a second scaled time series of data values associated with the second cardiac cycle.

Determining model parameters may comprise determining model parameters of the model using a difference between the first and second scaled time series.

The model parameters may be determined, such that the determined difference is minimized.

In other words, the first and the second time series are scaled onto the reference cardiac cycle, i.e. to have the same cycle length, i.e. time length, as the reference time length of a reference cardiac cycle.

In general, a series of data values associated with a cardiac cycle is scaled, i.e. modified, by applying a model to the time series, whereby a scaled time series data values associated with the cardiac cycle is generated. By applying the trained model to a time series, at least one data value of the scaled time series may be associated with a different time value, or in general index value. In various examples, a scaled time series may refer to a time series with a modified time scale, i.e. scaled time or index values, such that the time length of the first and second scaled time series may be the same, and may be same as the time length of the reference cardiac cycle. For example, a time length, i.e. time period or interval, defined by the first and last time values in the time series, or in one or more subsections of the time series may be scaled, i.e. the time length may be extended or shortened. Further, the scaled time series may be interpolated, wherein new data values within such a scaled time series or subsection of a time series may be associated with new time values, which may be determined by interpolation using a cardiac phase interpolation model containing fixed and scaled intervals according to the present disclosure.

It is to be understood that modifying the time scale, or in general index scale, may be necessary to normalize all cardiac cycles to the same cycle length. However, either the time scale can be changed and the data values can be kept fixed, or the time grid can be kept fixed and sample values can be interpolated or a mixture of both.

In various examples, the time series of data values associated with the reference cardiac cycle may be a time series of data values of a measurement signal of a cardiac cycle, in particular one of the plurality of cardiac cycles over which the measurement is performed, or an averaged time series of data values from measurement signals of least two different cardiac cycles of the plurality of cardiac cycles, in particular of the first and the second time series. For example, data values of corresponding time or index values may be an average of the respective data values of the respective individual time series of cardiac cycles.

In another step, the model is trained using the first and/or the second scaled time series and/or a time series of data values associated with the reference cardiac cycle.

In various examples, a difference between the scaled time series associated with the first cardiac cycle and the scaled time series associated with the second cardiac cycle may be determined by determining a difference between data values of the first scaled time series associated with the first cardiac cycle and corresponding data values associated with the reference cardiac cycle and/or the second scaled time series. For example, corresponding data values may have substantially the same time/index value, or within predefined upper and lower limit deviations from the same time/index value, in other words, they may lie in a same time interval relative to the beginning of the respective cardiac cycle.

The model may be trained such that the difference between the time series of data points is minimized. All data points, more than 10, 100, or 200 data points may be used for each time series to determine the difference and determine the model parameters. When the difference is minimized, the time series may have the same time length and/or a similar measurement signal. Accordingly, time series used to train the model may be scaled such that they extend over the same period of time.

The first and/or the second time series and/or the time series of the reference cardiac cycle may comprise data values of a measurement signal of a respective cardiac cycle including signal characteristics caused by a cardiac movement of a patient, in particular an Electrocardiography (ECG) measurement signal of a patient.

The first and/or the second time series, and/or the time series of data points associated with the reference cardiac cycle, may include a Magnetohydrodynamic (MHD) effect in a patient, in particular comprise data values of a measurement signal of the respective cardiac cycle including signal characteristics caused by a Magnetohydrodynamic (MHD) effect in a patient. In various examples, the characteristics in time series caused by a Magnetohydrodynamic (MHD) effect may be used to determine the model parameters.

The present disclosure is based on the concept that a signal representing cardiac motion over a plurality of cardiac cycles can be used for determining model parameters of a model for cardiac phase interpolation. For each cardiac cycle, a plurality of data values of a time series is used, for example more than 10 data values of a measurement signal per cardiac cycle, in contrast to conventional methods which may use parameters extracted from a measurement signal, for example a time value describing the duration of the cardiac cycle or a trigger point of time of a cardiac cycle.

Thereby, the method according to the present disclosure enables a more reliable and more precise determination of start and end times of cardiac phases in a cardiac cycle even in patients with strong cardiac arrhythmia.

A medical system, for example a Magnetic Resonance Imaging (MRI) system acquiring data over multiple cardiac cycles for cine scans, gated SPECT methods, or any other method acquiring data over multiple cardiac cycles, is configured to carry out a method according to the present disclosure. A medical system may comprise a control unit and a memory unit, wherein the memory unit stores control information executable by the control unit, and wherein the medical system is configured to perform any method or combination of methods according to the present disclosure.

A computer program, or computer program product, which is directly loadable into a control unit of a medical system, comprises instructions which, when the program is executed by the control unit of the medical system, cause the medical system to execute the steps of any method or combination of methods according to the present disclosure.

An electronically readable data carrier comprises electronically readable control information stored thereon, which is configured such that, when executed in a control unit of a medical system, it causes the medical system to execute the steps of any method or combination of methods according to the present disclosure.

For such a medical system, control unit, computer program and an electronically readable data carrier, technical effects may be achieved which correspond to the technical effects for the methods according to the present disclosure.

Although the specific features described in the above summary and the following detailed description are described in relation to specific examples, it is understood that the features may not only be used in the respective combinations, but may also be used in isolation or in any combination, and features, which are described in the context of different methods, medical systems, computer programs and electronically readable media may be combined and correlated with each other, unless expressly stated otherwise.

The above summary is therefore only intended to give a brief overview of some features of some embodiments and implementations and is not to be understood as a limitation. Other embodiments may include features other than those described above.

BRIEF DESCRIPTION OF THE DRAWINGS

The present disclosure is described in more detail below with reference to the accompanying drawings, in which like reference numerals refer to like elements.

FIG. 7 schematically illustrates the superimposed measurement signals of the cardiac cycles after linear interpolation of each entire cardiac cycle to an average (i.e. reference) cardiac cycle.

FIG. 8 schematically illustrates the superimposed measurement signals of the cardiac cycles after linear interpolation with a fixed (i.e. not temporally scaled) 450 ms region at the start and a 50 ms fixed region before the end of each cardiac cycle.

FIG. 9 schematically illustrates the superimposed measurement signals of the cardiac cycles of channel 1, without interpolation (as in FIG. 5), after linear interpolation (as in FIG. 6), and after linear interpolation starting after 400 ms from the beginning of each cardiac cycle and with a 50 ms stop region before the end of each cardiac cycle.

FIG. 10 schematically illustrates a flowchart with steps for determining model parameters for cardiac phase interpolation, according to embodiments of the present disclosure.

FIG. 11 schematically illustrates a medical system with which the methods for determining model parameters for cardia phase interpolation may be carried out, according to embodiments of the present disclosure.

DETAILED DESCRIPTION

Figure 1:
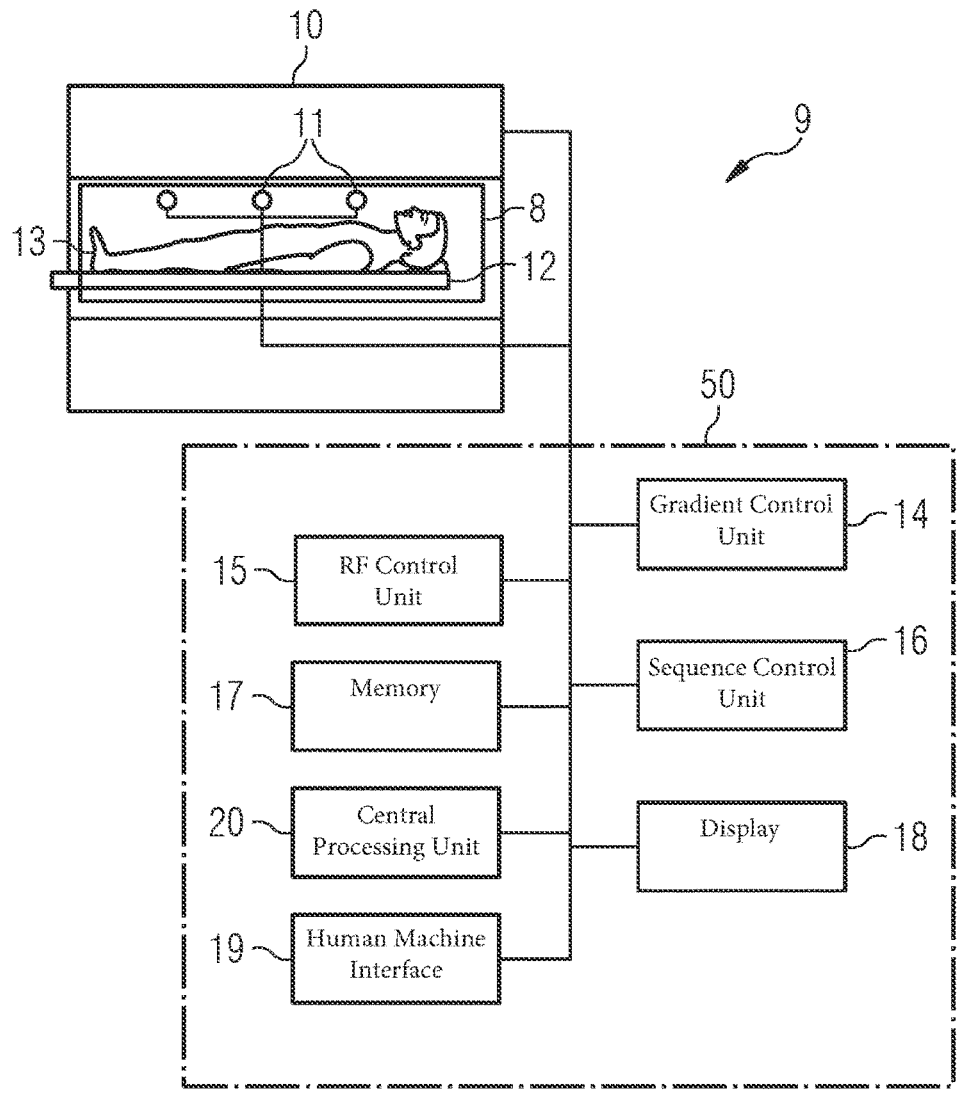
FIG. 1 shows a schematic view of an MR imaging system configured to generate MR images of the heart and to assign them to different phases of the cardiac cycle.

The above-mentioned elements, features, steps, and concepts according to the present disclosure will be explained in the following detailed description in the context of exemplary embodiments, which are explained with reference to the attached drawings.

The drawings are to be regarded as schematic drawings and the elements depicted in the drawings are not necessarily shown to scale. Rather, the various elements are presented in such a way that their function and general purpose may be understood by a person skilled in the art. Any connection or coupling between functional blocks, devices, components or other physical or functional units described in the drawings or herein may also be made by indirect connection or coupling. A coupling between the components may also be established via a wireless connection. Function blocks may be implemented in hardware, firmware, software, or a combination thereof.

It should be noted that the following description of the execution examples is not to be understood in a narrow sense. The scope of the present disclosure shall not be limited by the examples described in the following or by the drawings, which are for illustration purposes only.

Cardiac MRI requires synchronization with cardiac motion to avoid image artefacts like blurring or phase-encode ghosting of cardiac tissue. Conventionally, for synchronization a trigger signal approximately correlated to cardiac motion is used. This signal can be generated by different sources. In clinical use it is usually the ECG, or Photoplethysmography if necessary, as this is markedly inferior for reasons given later. More experimental techniques exist, e.g., acoustic triggering or Pilot Tone, as described in document EP 3 413 075 A1.

Cine imaging generates an apparent movie loop over the cardiac motion phases (CPh). However, it is important to understand that this is not usually a "real-time" movie. For sufficiently fine spatiotemporal resolution (which is one of the main "selling points" of CMR's "gold standard" clinical reputation), the standard in clinical use is to acquire the data over typically 4-7 cardiac cycles during a breath hold, by acquiring a fraction of the required raw data in each cycle. For image reconstruction the blocks are combined to form a series of complete data sets for each timing after the trigger, complete enough to reconstruct an image series from them. The task is to combine data that corresponds to the same cardiac motion phase so that the series of these sets can support accurate measurement of cardiac function, while also being clear enough to give clinically useful reports on wall motion abnormalities, flow disturbances, valve diseases, etc which under ideal patient conditions is the "gold standard" imaging of cine CMR.

Thus, data blocks or segments corresponding to the same CPh must be determined. If a high quality continuous monitoring of the cardiac phases for every heart beat is available—sources could be ultra-sound measurements, as described in U.S. Pat. No. 7,945,304 B2, or Pilot Tone—then the CPh can be determined from these monitoring signals directly.

However, these signals are typically not available with sufficient quality and thus a model f(TT,RR) that maps from TT to CPh in each cardiac cycle interval RR must be used. This model can also be seen as a cardiac cycle specific correction of the TT, i.e., an interpolation from measured TT to normalized TT(NTT) where NTT is adapted to a representative, i.e. reference, mean cardiac cycle duration (MCD) which itself is derived over the duration of the breath-hold e.g., the mean or median value of all CCD during the breath-hold.

FIG. 1 shows a schematic view of an MR imaging system 9, which comprises a magnet 10 generating the magnetic field B0 and which can generate the MR images of the heart which should be assigned in a retroactive gating to the different cardiac phases of the cardiac cycle. The patient or object under examination 13 lying on a table 12 is moved into the center of the MR imaging system 9, where the MR signals can be detected after excitation by RF pulses using coils 11. By applying RF pulses and magnetic field gradients, the nuclear spins of object 13, especially the part located in the receiving coils are excited and location coded currents induced by spin precession can be detected. The way how MR images, especially CINE images are generated and how the MR signals are detected, using a sequence of RF pulses and a sequence of magnetic field gradients, is known in the art, so that a detailed explanation thereof is omitted. The MR system may furthermore comprise shim coils 8 which are used to correct in-homogeneities of the magnetic field B0.

The MR imaging system 9 comprises a control module 50 which is used for controlling the MR imaging system. The control module 50 comprises a gradient control unit 14 for controlling and switching the magnetic field gradients, an RF control unit 15 for controlling and generating RF pulses for the imaging sequences. The image sequence control unit 16 is provided to control the sequence of the applied RF pulses and magnetic field gradients and thus is also configured to partly control the gradient control unit 14 and the RF control unit 15. In a memory 17, computer programs needed for operating the MR imaging system and the imaging sequences necessary for generating the MR images can be stored together with the generated MR images. The MR images and any further information can be displayed on a display 18 wherein a human machine interface 19 is provided, which can be used by an operator of the MR imaging system to control the MR imaging system. A central processing unit 20 can coordinate the operation of the different functional units shown in FIG. 1 and can comprise one or more processors, which can carry out instructions stored on the memory 17. The memory can include program code to be executed by the processing unit 20.

In the following, the different steps carried out during the assignment of the MR images to the different phases are discussed in more detail.

In the example below, an interpolation model is discussed to reduce the dimensionality of the interpolation problem. The simplest choice is based on [Chung2004] and [Chung2012]: A two interval model is selected with one interval of constant duration, also called additional time interval, and one interval scaling with RR for an arbitrary trigger time point at a time TP0 after the P-wave, also called variable time interval. Relative to a trigger at an arbitrary point in the cardiac cycle during the first interval that does not coincide with the P-wave, the cardiac cycle is divided in at least 3 intervals (2 interpolation periods and the variable time interval) with different interpolation rules.

Model Selection

Figure 2:
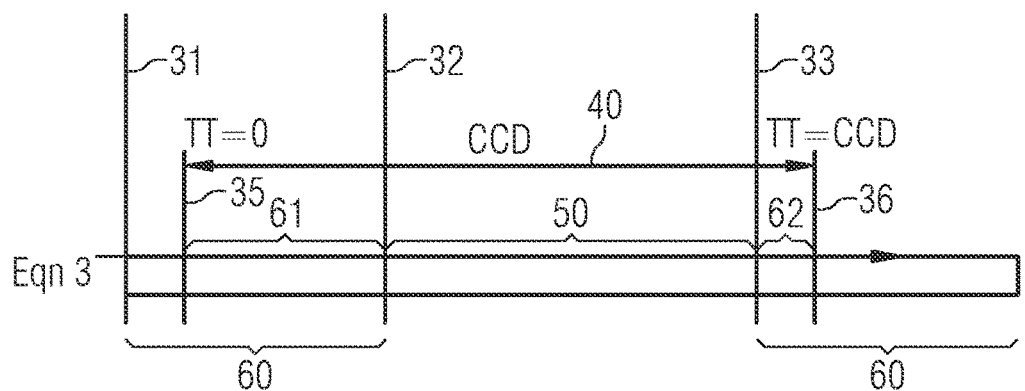
FIG. 2 shows a schematic view of a model used to assign the MR images to the different heart phases.

FIG. 2 shows a cardiac cycle and how a model is used with a variable time interval that the cycle begins at the trigger time point TT=0 with a weakly scaling interval followed by a linearly scaling interval and ends again with a weakly scaling interval.

FIG. 2 shows the lengths of the cardiac cycle 40 as determined by the R wave of the ECG signal. The two R waves are shown by the time points 35 and 36. Furthermore, the P wave 31 of the ECG signal, the end of the E wave, e.g. determined from an ultrasound signal is shown by 32 and the P wave 33 as determined from the ECG signal is indicated. The model is based on a variable time interval 50 and a constant or additional time interval 60. Based on the trigger points, the cardiac cycle comprises a first interval 61 which is more or less independent of the cardiac cycle, the variable time interval 50 and a part of the consecutive constant time interval, the interval and 62.

Figure 3:
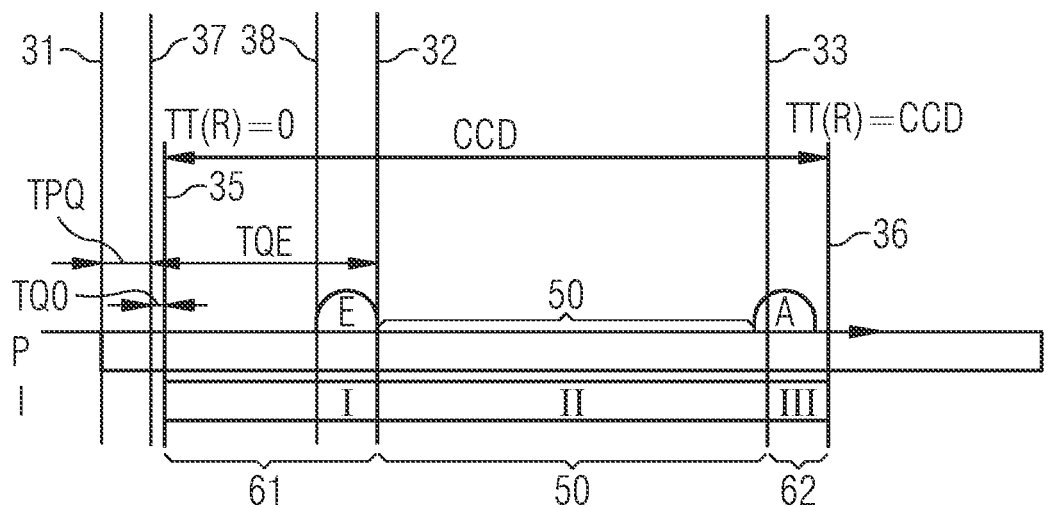
FIG. 3 shows a more detailed view of the model of FIG. 2 and the calculation of the duration of the variable time interval occurring in the cardiac cycle.

FIG. 3 and the following equation 3 set these intervals or intervals in relation to the physiologic events as seen by ultra-sound and diagnostic ECG. In addition to the time points 31, 32 and 33, discussed in connection with FIG. 2, the following time points are shown: the ECG Q wave 37, and the end of the ECG T wave 38.

FIG. 3 shows the physiological periods P and the interpolation periods I.

$$
\begin{aligned}
\text{CPh} = \{ & \\
& TT(R)/\ MCD; && \text{for } TT(R) < T0E, \\
& ((TT(R) - T0E) * (MCD - TPE) / (CCD - TPE) + T0E\ ) / MCD \\
& \quad \text{for } T0P > TT(R) > T0E \\
& (TT(R) - T0P) / MCD + \text{maxScaledPhase} && \text{for } TT(R) > T0P \\
& \quad \text{with} \\
& \text{maxScaledPhase} = ((T0P - T0E) * (MCD - TPE) / (CCD - TPE) + T0E\ ) / MCD; \\
\} & && \text{Equation [3]}
\end{aligned}
$$

With
CCD=cardiac cycle duration of the current heartbeat
MCD="average", e.g., mean or median cardiac cycle length over the measurement
T<A><B>=time from event <A> to event <B>
0=trigger time point
E=(end of) ultra-sound E-wave
A=(start of) ultra-sound A-wave
P=ECG P-wave
Q=ECG Q-wave The following relationships hold:
T0E=TQE−TQ0=duration of interval I, shown by reference numeral 61
TP0=TPQ+TQ0=duration of interval III, shown by reference numeral 62
TPE=TPQ+TQE=weakly scaling interval shown by reference numeral 60
TEP=CCD−TPE=linearly scaling interval (diastasis 50)

$$T0E = TQE - TQ0$$

$$T0P = CCD - TP0 = T0E + TEP$$

The model is parametrized fully with the measured cycle durations CCD and MCD and 2 timing parameters. One useful choice for these two parameters would be a purely physiologic parameter, e.g., TPE, giving the total duration of the weakly scaling interval 60 parameter, plus a parameter that contains besides physiological information all system specific times, e.g., TP0 specifying the position of the trigger in the cardiac cycle (from the P-wave as its notation implies). The system specific part of the second parameter can be predetermined once the triggering algorithms have been fixed.

If heartbeats occur with CCD<T0E, they can either be rejected as being non-representative or incorrectly triggered or scaled according to equation 1.

Rough values for the parameters are
TQE ~400 ms (−100 ms, i.e. ½ E-wave duration*)
TPQ ~150 ms (−70 ms, i.e. ½ A-wave duration*)

Transition between the intervals does not occur instantaneously but occurs smoothly over a time period. Thus, a conservative estimate of their duration should be applied.

Thus, for the model with predetermined constants, we would apply only half their duration (~100 ms for E-wave and ~70 ms for A-wave.)

A further refinement of the parameter choice could take into account that parameters scale with average RR as described in [Chung2003].

These parameters could be used as starting values or to specify a value range for a parameter optimization algorithm.

Alternative Models:
1. Because the underlying mechanical motion can be smooth, the separation into 3 regions with different interpolation rules is just an approximation to the smooth variation likely to occur in reality, so the transitions between regional rules could be gradual rather than instant.
2. a general smooth interpolation rule, e.g., described by splines
3. a closed equation, e.g., arctan(f(TT/CCD))

Measure Model Data

The parameters for the interpolation model are derived from information recorded in the MR scanner. All data that represents cardiac motion and is thus subject to the same scaling rules can be used. This data can be physiological data like ECG, pulse, PT or acoustic signals, or MR imaging data or a combination thereof. Preferably, the data is measured simultaneously with the cine measurement.

This results in an important advance offered by this invention: the interval guidance is measured per heartbeat used and in real-time simultaneously with the cine measurement.

Determine Model Parameter

The physiologic contribution to the parameters can be determined in multiple ways:

a) Parameters from Measured Data

Physiologic monitoring signals like Pilot Tone or MR-navigators or -images can be evaluated for interpolation. Methods for data analysis include
running trial reconstructions using interpolations over a predetermined range of parameters and maximizing image sharpness.
apply equation 2 to physiologic or imaging data, running it forward and backward in time and comparing the resulting signals or images for differences to determine the start and end point of the linear scaling interval.
or a combination of the above methods on different signals b) Literature Parameters The values from literature could be coupled to a measured parameter, e.g., they could be a function of heart rate (prior art) or known clinical condition (new). Literature values can be used as start or boundary values for model fitting, and as model values for a subset of model parameters, e.g., in case of insufficient data quality to determine all model parameters.

c) Interactive Parameters

Finally, the user can override internal parameter values in situations where the user has additional more accurate information, e.g., from ultra-sound, diagnostic ECG or high-resolution MR cine measurements.

Apply Parametrized Model

MR data contains for every readout the time-after-trigger TT. The model is applied to these timestamps to map MR data from different cardiac cycles to a common coordinate system, i.e., the cardiac phase CPh.

Inaccuracies of the model and its parametrization could result in interpolation errors that cause inconsistencies between the data from different heartbeats. This will result in image artefacts like blurring or ghosting. These interpolation errors increase with time from the trigger point. Using standard forward interpolation these errors could thus affect the late diastolic images most. These errors can be minimized by keeping the interpolation distance small. Interpolating backward from the end of the cardiac cycle instead of forward from the beginning, the error can be minimized in the late diastolic portion of the cardiac cycle. Thus, it is beneficial to apply both interpolation directions and merge the results from both interpolation directions. Interpolation can be achieved by forming a weighted average of the resulting values for CPh with smoothly varying weights across the cardiac cycle.

More options how the physiological parameter is deduced from the acquired data are described in the application having the title "Using cardiac motion for training a cardiac phase" from the same inventors as the present application and filed on the same day as the present application.

Figure 4:
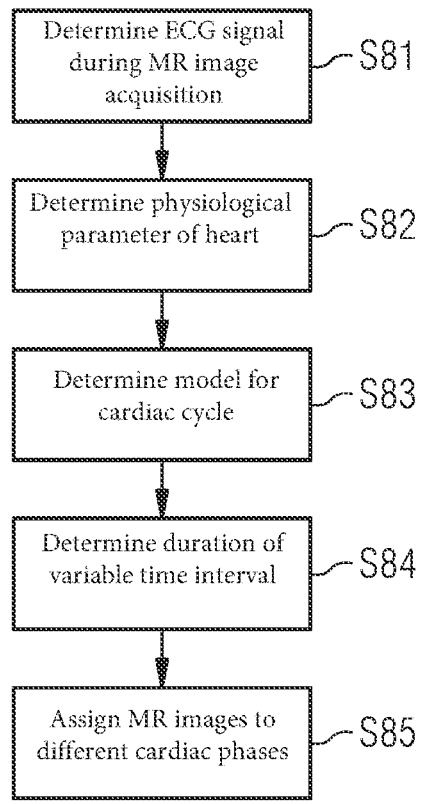
FIG. 4 shows a schematic view of a flowchart comprising the steps needed for assigning the MR images to the different phases of a cardiac cycle.

FIG. 4 summarizes some of the steps which are carried out in the method discussed above.

In step S 81 that ECG signal is determined during the acquisition of the MR images which are obtained at the different cardiac cycles. Furthermore, in step S 82, at least one physiological parameter of the heart is determined during the acquisition of the MR images which are obtained at the different cardiac cycles. Furthermore, in step S 83 a model is determined for the cardiac cycle including the variable time interval of variable duration and at least one additional time interval having a lower variability. The additional time interval can be a constant time interval. In FIG. 2 the consistent time interval 60 and the variable time interval 50 are shown. The duration of the variable time interval is determined in step S 84 based on the physiological parameter and in step S 85 the MR images are assigned to different cardiac phases taking into account the duration of the variable time interval and the duration of the cardiac cycle in each of the cardiac cycles.

In connection with FIGS. 5 to 11 methods are discussed in further detail how the parameters governing the separation into the three regions I to III of each cycle shown in FIG. 3 could be found.

A diagnostic ECG contains multiple waves during the cardiac cycle: the QRS complex that indicates the electrical activation of the ventricular contraction, the T wave that indicates the end systolic "repolarization" interval of the ventricle and late in the cardiac cycle the P wave that indicates the start of the atrial contraction. These waves can be used as markers to separate the weakly and strongly scaling cardiac cycle intervals. The P-wave corresponds to the start of the weakly scaling interval, but there is no clear electric activity marking the precise end of this interval (approximately around the end of the T-wave). Therefore, even a diagnostic quality ECG could not be used by itself to determine the model parameters.

The linear scaling interval ('ventricular diastasis') is starting with the end of the ultra-sound E-wave and ends with the start of the ultra-sound A-wave. Therefore, an ultrasound measurement would provide the information we are interested in. However, it is highly challenging to obtain ultra-sound compatibly with MRI and it is far from routinely available in commercial MR scanners.

In the MRI environment, the ECG is degraded as explained below, and is conventionally used only to generate a trigger signal at the R-wave of the cardiac cycle. Thus, its quality can be limited and typically only the R-wave is routinely detected; however, the other components present in the signal may yield valuable information about the patient's cardiac cycle as well.

Detrimental effects that generate additional artefact waves on the ECG are:

MRI gradient pulses that generate spike-like signal that obscures subtle signals. This is especially problematic for non-periodic sequences with strong spoiler or encoding gradients (e.g., for diffusion or other preparation pulses). They are present only during measurements and for many measurements, especially the cine and cine flow scans which are the main targets of this invention, their contribution to the signal is approximately constant and thus negligible.

The strong static magnetic field of the magnet in an MRI scanner leads to the magneto hydro dynamic effect (MHD): Flowing blood across the magnetic field will generate an electric field that is proportional to the flow velocity, which always but with varying amplitude is detected in the ECG channels. The MHD is superimposed on the true ECG signal and presents itself as a series of extra pulses or oscillations during each normal cardiac cycle. This effect increases with field strength: it is visible at 1.5 T, but at 3 T can reach amplitudes comparable to the R-wave amplitude. In triggering algorithms the R-wave can be detected despite these effects because the R-wave is usually sharper in time. The strength of voltage detected from each major pulse of blood flow depends on its angle to B0 and the conductance from its location to the ECG pads, which will be further convoluted with variations in patient anatomy as well. Historically, in cardiac MRI these MHD pulses have previously been dismissed as a nuisance only that renders detailed features of the ECG in MR systems non-diagnostic.

Therefore, the MHD effect on the ECG does not necessarily originate in the heart itself, but can represent a superimposed voltage originating from blood in the blood vessels, which is induced by its flow in the main B0 magnetic field.

One idea is that any contribution in the ECG that is related to cardiac motion can be used to identify the scaling and constant intervals of cardiac motion during each individual cardiac cycle, as measurement data for the respective cardiac cycle becomes available, i.e. beat-to-beat. Gradient induced spikes are not directly linked to cardiac motion, but MHD is. Thus, the normally unwanted MHD can be used for this purpose. Together with the "true" ECG-waves it will provide a signal that can be analyzed to determine the interpolation model parameters.

Note on timing relationship of MHD and cardiac tissue motion: pulse wave velocity delays parts of the signal coming from aortic arch across B0 and usually the strongest signal by worst case 40 ms. However the main pulmonary artery flow also partially crosses B0, as do the smaller left and right branch PAs (though these perhaps have less "contact tissue" pathways towards the ECG pads), and further in a "horizontal heart" the ventricular outflows may be more across B0 than in some other patients. Thus, the detailed relationship of MHD and cardiac tissue motion is highly variable per subject and ECG pad positioning, but limited to delays that are typically smaller than the time resolution of the clinical Cine measurement to be corrected.

If a model for the scaling rule is assumed, e.g. equation [3], then the task is to find the free parameters of the model for each cardiac cycle of raw data that is assembled to complete the required raw data coverage. This can be achieved by recording ECG data over several heart beats, either during a measurement or during scanner idle times. If the recorded data contains cardiac cycles of different length, the ECG data for these cycles can be compared using cross correlation after applying the scaling rule. The simplest way to find the correct value for the free parameters is to do this comparison for all possible combinations of free parameter values and identify the combination that results in the highest correlation values.

Figure 5:
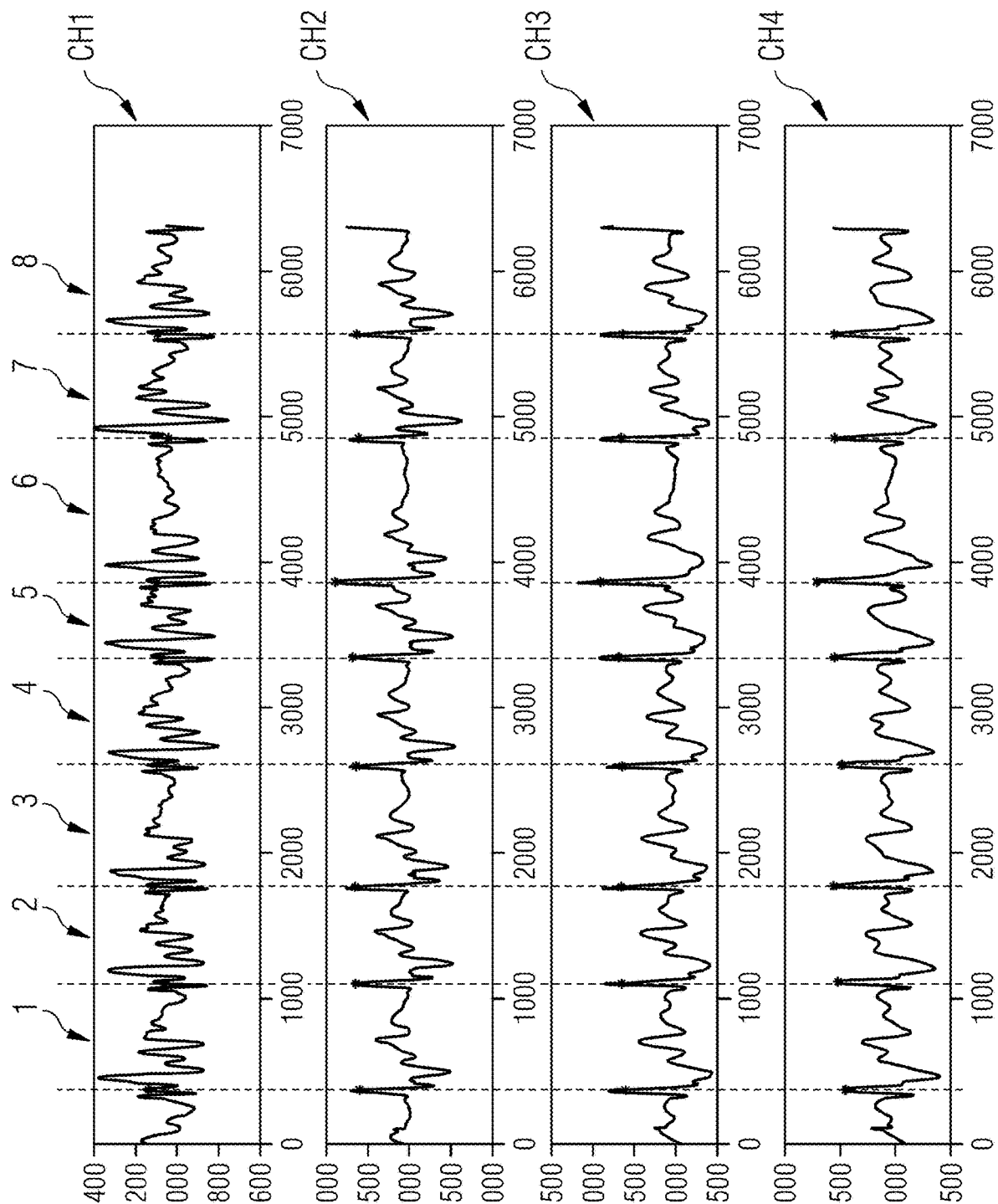
FIG. 5 schematically illustrates ECG measurement signals over eight cardiac cycles of four ECG channels, according to embodiments of the present disclosure.

FIG. 5 schematically illustrates ECG measurement signals over eight cardiac cycles 1-8 of four ECG channels CH1, CH2, CH3, CH4, according to embodiments of the present disclosure.

Measurement data values of these example time series are plotted against time in ms, wherein dotted lines indicate the trigger time point of each cardiac cycle. The magnetohydrodynamic effect is visible in all four channels CH1, CH2, CH3, CH4. As can be seen, the cardiac cycles 1-8 exhibit strongly varying cardiac cycle durations, wherein 5 is shortened and beat 6 prolonged.

Figure 6:
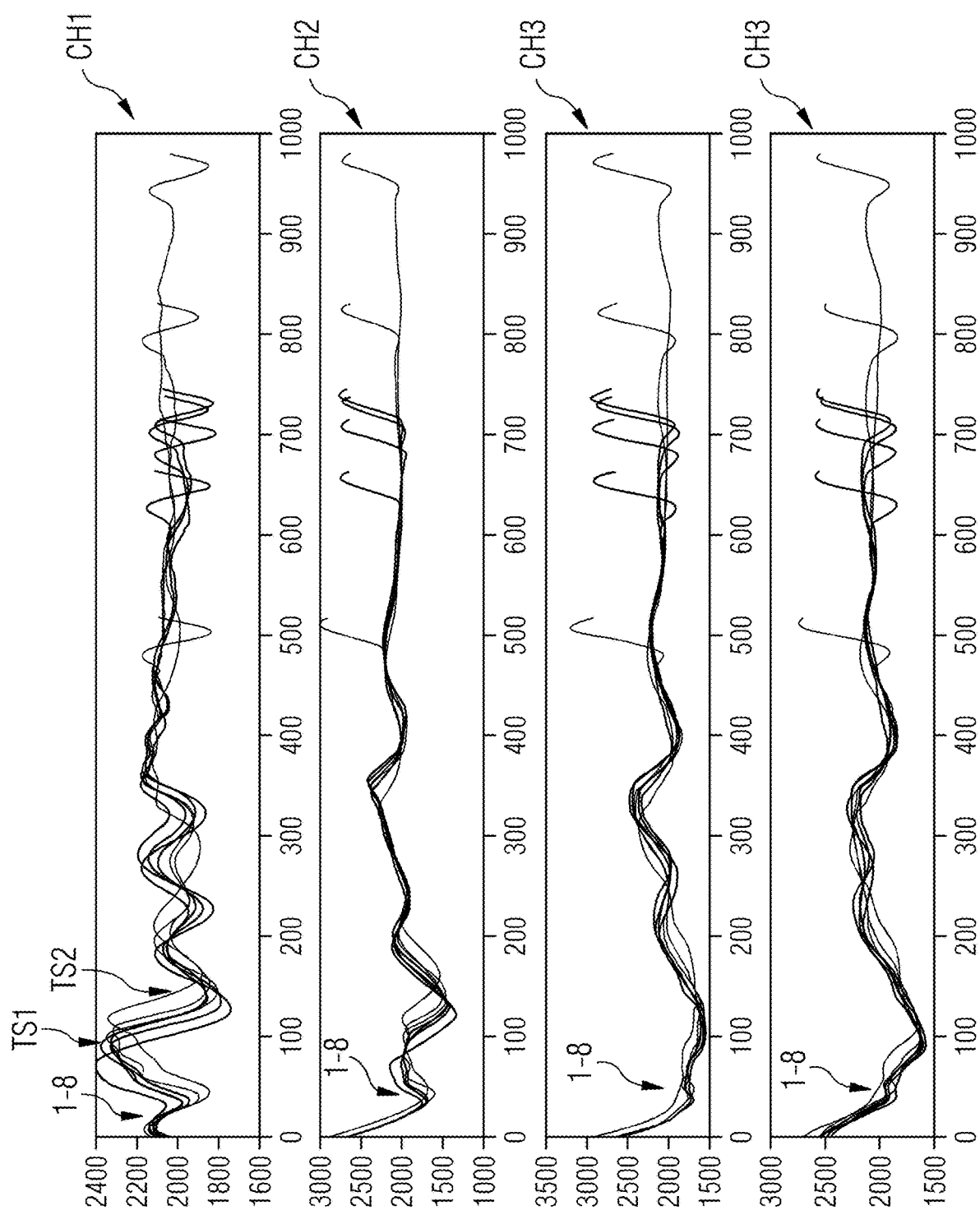
FIG. 6 schematically illustrates the superimposed measurement signals of the cardiac cycles of the four ECG channels, according to embodiments of the disclosure.

FIG. 6 schematically illustrates the superimposed measurement signals of the cardiac cycles 1-8 of the four ECG channels CH1, CH2, CH3, CH4.

As can be seen in FIG. 6, a plot of these signals relative to the R-wave, i.e. all cardiac cycles are plotted on top of each other, wherein the last incomplete heart beat has been omitted, and the data values are plotted against time-after trigger in ms. Two of the signals are marked as TS1 and TS1, and may refer to any two time series that can be used to train a model according to the present disclosure.

FIG. 7 schematically illustrates the superimposed measurement signals of the cardiac cycles 1-8 after linear interpolation of each entire cardiac cycle to an average (i.e. reference) cardiac cycle.

The last incomplete heart beat has been omitted, and the data is plotted after interpolation against time after trigger in an average cardiac cycle.

FIG. 8 schematically illustrates the superimposed measurement signals of the cardiac cycles after linear interpolation with a fixed (i.e. not temporally scaled) 450 ms region at the start and a 50 ms fixed region before the end of each cardiac cycle, according to embodiments of the disclosure.

FIG. 9 schematically illustrates the superimposed measurement signals of the cardiac cycles of channel 1, without interpolation (as in FIG. 5), after full-cycle linear interpolation (as in FIG. 6), and after linear interpolation starting after 400 ms from the beginning of each cardiac cycle and with a 50 ms stop region before the end of each cardiac cycle, according to embodiments of the disclosure.

Two of the scaled measurement signals after linear interpolation starting after 400 ms from the beginning of each cardiac cycle and with a 50 ms stop region before the end of each cardiac cycle are marked as SC-TS1, correlating to the measurement signal TS1 of FIG. 2, and SC-TS2, correlating to the measurement signal TS2 of FIG. 2.

The data demonstrates that a weakly scaling interval I is identifiable in the data in all channels, and that the weakly scaling interval III is identifiable in the data in all channels. The signals for the shortest and longest cardiac cycle 5 and 6 deviate from the signals for the other cardiac cycles. This difference could be used to separate arrhythmic from regular heart beats.

Additional Info by Vectorcardiography (VCG):

This ECG MHD information may be further identified using the VCG method of analyzing the multiple electrical channels recorded. The "direction" of MHD waves may assist in separating strongly delayed ones from ones more faithfully following cardiac motion, improving the parameter quality.

Additional Use of the MHD Effect Using VCG:

The separation of different MHD waves by VCG may also help identify certain kinds of abnormal beats of the heart such as ventricular ectopic beats. Specifically, the difference between ECG outside the field and within the field might be supportive of this invention. The ECG is already recorded outside the B0 field by the "training" stage which by rerunning inside B0 with no scan running (i.e. not overwriting the same training data, keeping this separate—unlike the current product) could provide that difference information. (However, a possible limitation may require attention because it is widely believed that the changing ECG pad skin contact resistance during a long CMR scan can alter the channel distributions of the ECG signal as the scan proceeds.)

The disclosed techniques newly employ MHD signals in the ECG that have previously been discarded, which contain cardiac blood flow data that may assist in combination with the conventional R-wave detection for optimizing non-uniform scaling of retrogated cine data.

This information can be gained during the scan to be corrected or from ECG data taken in the magnet before the scan.

Alternatively, the interpolation parameters could be obtained from motion information strongly present in the cardiac "Pilot Tone" data as described in EP 3 413 075 A1 and related ID).To optimize the interpolation of retrogated cines one could employ cardiac PT information in combination with the above MHD information and with the conventional ECG trigger. For example, ECG-R-wave based triggering could be used while PT data and optionally MHD could be used to derive interpolation information.

FIG. 10 schematically illustrates a flowchart with steps for determining model parameters for cardiac phase interpolation, according to embodiments of the present disclosure.

The method starts in step S10. In step S20, a first time series of data values associated with a first cardiac cycle is received. In step S30, the first time series is scaled to a reference time length of a reference cardiac cycle, wherein scaling comprises applying a model to the first time series, in order to generate a first scaled time series of data values associated with the first cardiac cycle. In step S40, the model parameters are determined using the first scaled time series, in particular a difference between the first scaled time series and another time series, such as the reference time series or another scaled time series. The method ends in step S50.

FIG. 11 schematically illustrates a medical system 100 with which the methods for determining model parameters for cardiac phase interpolation may be carried out, according to embodiments of the present disclosure.

A medical system 100 comprises a control unit 110 including a processing unit 120 and a memory unit 130, wherein the memory unit 30 stores control information executable by the processing unit 120, and wherein, when executing of the control information in the processing unit 120, the medical system 100 is configured to perform a method according to the present disclosure.

Advantages of the Disclosed Techniques Include:

Cardiac phase interpolation is optimized for the individual patient automatically without the need for the user to repeat the measurement with multiple parameter settings. This will result in improved image quality in the presence of varying heart rate for retrogated cine images.

Evaluations that are based on multiple measurements, e.g., ventricular function, will have more consistent input data, thus should be more reliable in case of varying heart rate.

Detailed aspects of cardiac function such as wall motion abnormalities, valve disorders and atrial function will be imaged with increased reliability as many patients exhibit variations in R-R interval due to arrhythmia or associated with breath-hold maneuvers.

The optimized interpolation rule can be applied to subsequent measurements, e.g., to automatically place the acquisition into the mid-diastolic interval and keep it there for slowly changing heart rates.

In disease, there is very often mechanical dyssynchrony of ventricular contraction and relaxation. Although this is a challenge, one or more example embodiments of the present invention would nevertheless be expected to yield improvements to cine imaging compared to the conventional cine retrogating method. Further, the dyssynchrony is quite often subtle and small, even difficult for clinicians to be certain of, and so this invention might be expected to improve retrogated cine imaging so that these small dyssynchronous perturbations to uniform cardiac contractility and relaxation might be made more visible.

From the above said, some general conclusions may be drawn:

Various techniques according to the present disclosure may provide for identification of cardiac phases, wherein a measurement signal characterized or dominated by an MHD effect may be used.

The first and the second time series of data values may be Electrocardiography (ECG) measurement signals of a patient, wherein each time series includes a different cardiac cycle. The time series may include signal characteristics of a Magnetohydrodynamic (MHD) effect in a patient, and may be representative of a cardiac motion. The time series of data values representative of a cardiac motion or measurement signal may consist of, or represent, or be predominantly characterized by a Magnetohydrodynamic (MHD) effect in the blood vessels of a patient.

The first and second cardiac cycles may be chronologically directly sequential cardiac cycles.

Scaling the first and/or the second time series to a reference time length of a reference cardiac cycle may comprise adapting time values associated with the data values. In various examples, the time series of each cardiac cycle is scaled to to match that of the reference cycle.

The first and/or the second scaled time series may have the same cardiac cycle time length, after applying the model, as the reference cardiac cycle.

In addition to the first and the second time series, a plurality of further time series associated with a respective one of a plurality of further cardiac cycles may be used to train the model, in particular each including a different cardiac cycle with a varying, i.e. different, cardiac cycle length. The model may be applied to each of the plurality of time series, as the time series become available during measurement, in order to determine a cardiac phase interpolation model for the respective cycle.

The reference cardiac cycle may be a mean, median, minimum, maximum cardiac cycle length of the plurality of cardiac cycles used for determining the model parameters.

The method may further comprise interpolating at least one of the first and the second scaled time series, wherein interpolating comprises generating new data values for corresponding new time values.

In various example, the first unscaled time series may contain the measured data for the first cardiac cycle. By applying the model, the first scaled time series is obtained, which is scaled to have the same time length as the reference cardiac cycle. In this regard, the model may be the scaling rule onto the reference cardiac cycle. After the scaling by applying the model, the data may already lie on a reference time grid, for example of the reference cardiac cycle, but in various examples data points may not lie on the reference time grid. In this case, the data of two cardiac cycles must first be interpolated to a common time grid, usually the reference time grid, before determination of a difference between the time series may be performed. In general, the scaling model may map to a reference time grid, specifically that of the reference heartbeat, i.e. it may comprise the necessary interpolation as an optional step. It is to be understood that this optional interpolation onto the reference time grid may be performed with the scaled and unscaled time series.

A difference between the first and the second scaled time series may comprise a difference between corresponding data values, i.e. which have the same time or index value.

The model may be referred to as a cardiac cycle interpolation model.

The time series of data values may represent or may be characterized by a cardiac motion, in particular an Electrocardiography (ECG) measurement signal or an PilotTone reference signal representing cardiac movement in an MRI measurement.

Determining model parameters may comprise adapting at least one model parameter to minimize a difference between the first and/or second scaled time series and/or the time series of measurement data values of the reference cardiac cycle.

Applying the model to a time series of data values may modify a time period defined between the first data value and the time value and the last time value in the time series.

The time series of data values may be acquired, and/or the determining of the model parameters for cardiac phase interpolation may be performed, during per cycle adaptation of the acquired data for each cycle of an MRI imaging method.

The model parameters may be determined, in order to minimize the difference between the first and/or second and/or the time series of data points associated with the reference cardiac cycle.

The method may further comprise determining a cardiac phase using the model, for example applying the model to a time value, which may be a time after trigger of a cardiac cycle, in order to provide a scaled time value as output, and/or identifying a cardiac phase of the cardiac cycle based on the scaled, or scaled, time value.

In various examples, the model may be used for comparing two time values of different cardiac cycles, wherein by applying the trained model to one or more time values, the time values may be on the same time scale and may be directly compared. In such a way, when two scaled time values, which may be associated with respective measurement data, may be the same or may be in a predefined time window/period, the two time values may be associated with the same cardiac phase.

In various examples, the model may be applied to an MRI data set, in order to associate different subset of the MRI dataset to specific cardiac phases.

The model may receive as input a duration of the reference cardiac cycle, e.g. as defined by trigger time points determined based on a characteristic wave of an ECG signal, specifically the R wave of the cardiac cycles. The model may receive as input a time series of data values of the reference cardiac cycle, which may be a time series of averaged data values over a plurality of cardiac cycles.

A model may be used to determine a cardiac phase, wherein the model modifies a time value, which may be a time after trigger of a periodic signal, e.g. an ECG signal. The time point, which may be a time after trigger, may be scaled using/by the same model, which is used for scaling/modifying the time series of data values associated with a cardiac cycle.

The parameters governing the model (i.e. the fixed and varying fraction timings within each beat) may be repeatedly adjusted before and/or during and/or after a measurement process, which may be the measurement process generating the time series for training the model or a measurement process, such as an MRI measurement process, in which the trained model is used for determining a cardiac phase.

The time series representative of a cardiac motion may be acquired and/or the training of the model for cardiac phase interpolation may performed per cycle to an MRI imaging method. In such a way, the model may be determined per cycle, i.e. for each cycle.

In a method for acquiring an MRI image of a heart, a MRI image may be associated with a cardiac phase using a scaled time value determined by a method according to the present disclosure.

Summarizing, a method is provided for training a model for cardiac phase interpolation comprising beat to beat parameter optimisation for each individual cardiac cycle required to complete the scan, which enable fast and reliable identification of cardiac phases by using a plurality of values of a measurement signal encoding a movement of a heart during a cardiac cycle.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group)

that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present disclosure was illustrated and described with regard to certain preferred embodiments, equivalents and changes will be made by persons skilled in the art after reading and understanding the description. This present disclosure covers all such equivalents and modifications and is limited only by the scope of the attached claims.

What is claimed is:

1. A computer-implemented method, comprising:
   receiving a first time series of data values associated with a first cardiac cycle;
   scaling the first time series of data values to a reference time length of a reference cardiac cycle, the scaling including applying a model to the first time series of data values to generate a first scaled time series of data values associated with the first cardiac cycle;
   receiving a second time series of data values associated with a second cardiac cycle, at least one of the first time series of data values or the second time series of data values includes a Magnetohydrodynamic effect a patient;
   scaling the second time series of data values to the reference time length of the reference cardiac cycle, the scaling the second time series including applying the model to the second time series of data values to generate a second scaled time series of data values associated with the second cardiac cycle; and
   determining model parameters of the model based on a difference between the first scaled time series of data values and the second scaled time series of data values.

2. The computer-implemented method according to claim 1, wherein the determining determines the model parameters based on a difference between the first scaled time series of data values and a time series of data values associated with the reference cardiac cycle.

3. The computer-implemented method according to claim 1, wherein the reference cardiac cycle comprises:
   a time series of data values of a measurement signal associated with a third cardiac cycle, or
   an averaged time series of data values from measurement signals associated with at least two different cardiac cycles.

4. The computer-implemented method according to claim 1, wherein the first cardiac cycle and the second cardiac cycle are chronologically directly sequential cardiac cycles.

5. The computer-implemented method according to claim 1, wherein the at least one of the first time series of data values or the second time series of data values includes data values of a measurement signal, the measurement signal including signal characteristics caused by the Magnetohydrodynamic effect in the patient.

6. The computer-implemented method according to claim 1, wherein at least one of the first scaled time series of data values or the second scaled time series of data values has a same cardiac cycle time length as the reference cardiac cycle.

7. The computer-implemented method according to claim 1, wherein the reference cardiac cycle is one of:
   a mean cardiac cycle length of the first cardiac cycle a second cardiac cycle,
   a longest cardiac cycle among the first cardiac cycle among the second cardiac cycle, or
   a shortest cardiac cycle among the first cardiac cycle among the second cardiac cycle.

8. The computer-implemented method according to claim 1, further comprising:
   interpolating at least one of the first time series of data values, the second time series of data values, the first scaled time series of data values or the second scaled time series of data values, the interpolating including generating new data values for corresponding new time values within a scaled cycle time length.

9. The computer-implemented method according to claim 1, wherein at least one of
   the difference between the first scaled time series of data values and the second scaled time series of data values, or
   a difference between the first scaled time series of data values and a time series of data values associated with the reference cardiac cycle
   includes a difference between data values corresponding to a same time value.

10. The computer-implemented method according to claim 1, wherein the determining model parameters includes at least one of:
    determining at least one first model parameter among the model parameters to minimize the difference between the first scaled time series of data values and the second scaled time series of data values, or
    determining at least one second model parameter among the model parameters to minimize a difference between a time series of data values associated with the reference cardiac cycle and at least one of
    the first scaled time series of data values, or
    the second scaled time series of data values.

11. The computer-implemented method according to claim 1, wherein the model parameters are model parameters for a cardiac phase interpolation model of each of a plurality of cardiac cycles, and the model parameters are determined beat-to-beat.

12. The computer-implemented method according to claim 1, wherein the model comprises:
    starting parameter values including
    a length of a non-scaling time interval at a beginning of each cardiac cycle, and
    a length of a non-scaling time interval at an end of each cardiac cycle.

13. A medical system comprising:
    a memory storing control information; and
    at least one processor
    configured to execute the control information to cause the medical system to
    receive a first time series of data values associated with a first cardiac cycle,
    scale the first time series of data values to a reference time length of a reference cardiac cycle, the first time series being scaled by applying a model to the first time series of data values to generate a first scaled time series of data values associated with the first cardiac cycle,
    receive a second time series of data values associated with a second cardiac cycle, at least one of the first time series of data values or the second time series of data values includes a Magnetohydrodynamic effect in a patient,
    scale the second time series of data values to the reference time length of the reference cardiac cycle, the second time series being scaled by applying the model to the second time series of data values to generate a second scaled time series of data values associated with the second cardiac cycle, and
    determine model parameters of the model based on a difference between the first scaled time series of data values and the second scaled time series of data values.

14. The computer-implemented method of claim 3, wherein the averaged time series of data values is from measurement signals associated with the first time series of data values and a second time series of data values.

15. The computer-implemented method according to claim 5, wherein the measurement signal is an Electrocardiography measurement signal of the patient.

16. The computer-implemented method according to claim 8, wherein the new data values are associated with time values on a reference time grid of the reference cardiac cycle.

17. The computer-implemented method according to claim 11, wherein the determining the model parameters determines the model parameters of the cardiac phase interpolation model of each respective cardiac cycle among the plurality of cardiac cycles when measurement data for the respective cardiac cycle becomes available during a data acquisition over the plurality of cardiac cycles of an MRI imaging method.

18. A computer-implemented method, comprising:
receiving a first time series of data values associated with a first cardiac cycle;
scaling the first time series of data values to a reference time length of a reference cardiac cycle, the scaling including applying a model to the first time series of data values to generate a first scaled time series of data values associated with the first cardiac cycle;
receiving a second time series of data values associated with a second cardiac cycle, at least one of the first time series of data values or the second time series of data values including data values of a measurement signal, and the measurement signal being an Electrocardiography measurement signal including signal characteristics caused by a cardiac movement of a patient;
scaling the second time series of data values to the reference time length of the reference cardiac cycle, the scaling the second time series including applying the model to the second time series of data values to generate a second scaled time series of data values associated with the second cardiac cycle; and
determining model parameters of the model based on a difference between the first scaled time series of data values and the second scaled time series of data values.

19. A medical system comprising:
a memory storing control information; and
at least one processor configured to execute the control information to cause the medical system to
receive a first time series of data values associated with a first cardiac cycle,
scale the first time series of data values to a reference time length of a reference cardiac cycle, the first time series being scaled by applying a model to the first time series of data values to generate a first scaled time series of data values associated with the first cardiac cycle,
receive a second time series of data values associated with a second cardiac cycle, at least one of the first time series of data values or the second time series of data values including data values of a measurement signal, and the measurement signal being an Electrocardiography measurement signal including signal characteristics caused by a cardiac movement of a patient,
scale the second time series of data values to the reference time length of the reference cardiac cycle, the second time series being scaled by applying the model to the second time series of data values to generate a second scaled time series of data values associated with the second cardiac cycle, and
determine model parameters of the model based on a difference between the first scaled time series of data values and the second scaled time series of data values.

20. The computer-implemented method according to claim 1, further comprising:
generating a magnetic resonance imaging (MRI) data set using an MR imaging system; and
applying the model to the MRI data set.

21. The computer-implemented method according to claim 20, wherein
the generating the MRI data set includes MR signals detected based on a radio frequency pulse and a magnetic field gradient; and
the method further comprises displaying MR images corresponding to the MRI data set after the applying.

22. The computer-implemented method according to claim 20, wherein the applying the model to the MRI data set includes associating different subsets of the MRI data set to specific cardiac phases.

* * * * *